United States Patent
Delawter et al.

(10) Patent No.: US 6,525,819 B1
(45) Date of Patent: Feb. 25, 2003

(54) COLORIMETER FOR DENTAL APPLICATIONS

(75) Inventors: S. Brett Delawter, La Cañada, CA (US); Gregg A. Wagner, Boulder, CO (US); Gary Emerson, Golden, CO (US); Brian Franklin, Queen Creek, AZ (US)

(73) Assignee: PocketSpec Technologies Inc., Denver, CO (US)

( * ) Notice: Subject to any disclaimer, the term of this patent is extended or adjusted under 35 U.S.C. 154(b) by 0 days.

(21) Appl. No.: 09/365,438

(22) Filed: Aug. 2, 1999

Related U.S. Application Data (60) Provisional application No. 60/098,855, filed on Sep. 2, 1998, provisional application No. 60/098,845, filed on Sep. 2, 1998, provisional application No. 60/098,837, filed on Sep. 2, 1998, and provisional application No. 60/098,823, filed on Sep. 2, 1998.

(51) Int. Cl.[7] .................................................. G01J 3/50
(52) U.S. Cl. .......................... 356/406; 356/425; 433/29
(58) Field of Search ................................. 356/402, 405, 356/406, 407, 416, 419, 425; 433/26, 29; 250/226

(56) References Cited

U.S. PATENT DOCUMENTS

| | | | |
|---|---|---|---|
| 3,986,777 A | 10/1976 | Roll | 356/176 |
| 4,096,217 A | 6/1978 | Roll | 264/20 |

(List continued on next page.)

FOREIGN PATENT DOCUMENTS

| | | | | |
|---|---|---|---|---|
| DE | 19534517 A1 | * | 3/1997 | |
| EP | 367647 A1 | * | 5/1990 | |
| ES | 2113826-A! | * | 5/1998 | |
| JP | 4-338465 | | 11/1992 | A61C/19/04 |
| JP | 5-243541 | | 9/1993 | H01L/27/14 |

Primary Examiner—F. L. Evans
(74) Attorney, Agent, or Firm—LeBoeuf, Lamb, Greene & MacRae, L.L.P.; Gayle L. Strong; Elizabeth Stanley (57) ABSTRACT

The invention is a colorimeter for dental applications comprising a hand-held probe, similar in size to a dental drill, attached by an electrical cable to a small self-contained display module. The calorimeter provides the capability for measuring the colors of a number points along a line on the surface of an object such as a tooth. A measurement is made while placing the tip of the probe against, or in close proximity to, the surface of the object. The display module to which probe attaches contains a microprocessor and provides a control, display and data interface to the operator. The display module can be adapted for fastening to the wrist of the operator thereby leaving both hands free to manipulate the probe and other tools. The calorimeter is particularly well suited for measuring the color of teeth in a dentist's office in preparation for making dental prostheses which accurately match the color of natural teeth. The colorimeter generates from a single measurement an array of color data points measured along a line on the surface of an object. From those data points, the processor can perform statistical analysis yielding a single color value, generate and display a color profile along a surface, compare measured values with a preloaded table of values, or upload color data to a remote location for laboratory or manufacturing purposes. The colorimeter can also use variations in the color values measured along a line to identify boundaries of areas on a surface. For example, the color profile can be used to identify the gum line on a tooth. The probe comprises multiple light emitting diodes (LEDs) for successively emitting light of different colors toward a surface, a linear photosensor array for receiving light reflected from the surface, and a lens for directing light from the target to the array, all contained within the probe itself. The calorimeter may also comprise a cradle for storing the probe and display module when not in use. The cradle may provide a battery charger, calibration references, and data links for uploading or downloading data from a remote location.

36 Claims, 8 Drawing Sheets

U.S. PATENT DOCUMENTS

| | | |
|---|---|---|
| RE31,290 E | 6/1983 | Moore et al. .................. 128/6 |
| 4,654,794 A | 3/1987 | O'Brien ...................... 364/413 |
| 4,836,674 A | 6/1989 | Lequime et al. ............ 356/319 |
| 5,027,138 A | 6/1991 | Gandrud ...................... 354/62 |
| 5,383,020 A | 1/1995 | Vieillefosse ................ 356/326 |
| 5,428,450 A | 6/1995 | Vieillefosse et al. ........ 356/405 |
| 5,503,559 A | 4/1996 | Vari .......................... 433/224 |
| 5,527,262 A | 6/1996 | Monroe et al. ............. 600/110 |
| 5,690,486 A | 11/1997 | Zigelbaum ................... 433/29 |
| 5,691,701 A | 11/1997 | Wohlstein et al. .......... 340/603 |
| 5,739,915 A | 4/1998 | Gau et al. ................... 356/406 |
| 5,745,229 A | 4/1998 | Jung et al. .................... 356/73 |
| 5,759,030 A | 6/1998 | Jung et al. .................... 433/29 |
| 5,760,929 A | 6/1998 | Ichikawa et al. ........... 358/518 |
| 5,766,006 A | 6/1998 | Murljacic .................... 433/26 |
| 5,838,451 A | 11/1998 | McCarthy ................... 356/406 |
| 5,844,680 A | 12/1998 | Sperling ..................... 356/303 |
| 5,851,113 A | 12/1998 | Jung et al. .................... 433/29 |
| 5,871,351 A | 2/1999 | Jung et al. .................... 433/29 |
| 5,883,708 A | 3/1999 | Jung et al. .................... 356/73 |

\* cited by examiner

COLORIMETER FOR DENTAL APPLICATIONS

CROSS REFERENCE TO RELATED APPLICATIONS

This application takes priority under 35 U.S.C. §119 (e) to U.S. provisional applications having Ser. Nos. 60/098,823, 60/098,837, 60/098,845 and 60/098,855, all filed on Sep. 2, 1998, and all of which, along with co-pending application, Ser. No. 09/365,193 filed simultaneously herewith, are incorporated in their entirety by reference herein to the extent not inconsistent herewith.

FIELD OF INVENTION

This invention relates generally to devices and methods for the measurement of the color and reflectance of a tooth. The invention also provides for selecting a color and reflectance for a dental prosthesis which most closely matches that of the natural tooth.

BACKGROUND OF THE INVENTION

The conventional method of determining a color to use in the manufacture of a dental prosthesis is to use a number of comparison samples. The samples are held up to the patient's teeth surrounding the location where the prosthesis will be placed and the sample most closely matching the color of the teeth is chosen by visual observation. The difficulty in obtaining the optimum color match by this method is due to several factors which include the color and intensity of the light illuminating the comparison, the experience and visual acuity of the person making the comparison, and the use of a limited number of samples.

A standard, unambiguous system for measuring tooth colors is needed. Such a system should provide for accurate and repeatable color measurements in different environments such as various dentists' offices and manufacturers' laboratories. High-resolution color measurement data can then be provided to prosthesis manufacturers to ensure an optimum color match between a prosthesis and its surrounding natural teeth.

A number of previous inventions useful for measuring tooth colors have been patented. Some describe apparatuses for making color measurements and others describe methods for making measurements and using the results in the manufacture of artificial teeth. Several such inventions are briefly described in the following paragraphs.

U.S. Pat. No. 5,690,486, teaches a device for detecting the color of a damaged tooth and determining a color-matched restorative material. It describes the use of multiple LEDs for successively emitting light of different colors toward a target and a light sensor for receiving light reflected from the target, all contained within a hand-held, battery powered device. The device uses a fiber optic wand to convey light between the device and the tooth.

U.S. Pat. No. 5,739,915 describes as prior art a document-scanning system having a set of RGB light sources, a self-focus lens array (SLA) comprising a single row of rod lenses, and a single-row photosensor array. In operation, the light sources of each color are sequentially illuminated and light reflected from the document is focused by the lens onto the photosensor array. A set of electrical signals corresponding to each element of the array is produced by the array for each of the RGB colors. The RGB signals are then combined for subsequent color reproduction.

U.S. Pat. No. 5,838,451 discloses an apparatus for the measurement of spectral reflectance or spectral absorbance of an object or a material. The reflectance apparatus comprises multiple LEDs surrounding a photosensor, all mounted on a common substrate, and a lens for coupling light to and from the object.

U.S. Pat. No. 5,844,680 also discloses an apparatus for measuring and analyzing spectral radiation. It discloses three embodiments comprising: (1) multiple LED light sources with a single sensor, (2) a single light source with multiple sensors, and (3) multiple sources and sensors.

U.S. Pat. No. 5,851,113 discloses a system comprising a probe containing a plurality of optical fibers connected to a color measurement system. The patent describes various means of color measurement, including multicolored light sources (red, green, blue=RGB), and various analysis techniques.

U.S. Pat. No. RE 31,290 describes an imaging system comprising a rectangular photosensor array and a lens contained in a small probe connected to the system by a fiber optic bundle. Three light sources produce red, green, and blue light in sequence. Light is conducted from the sources through the fiber optics to the probe tip and reflected from the object of interest back through the lens to the array in the probe.

U.S. Pat. No. 5,766,006 teaches a system comprising an intraoral camera connected to a shade analyzer subsystem. The patent discloses a camera comprising either a single or a triple charge coupled device (CCD) array for capturing an image of the tooth in three (RGB) colors.

U.S. Pat. No. 5,760,929 discloses an image processing apparatus for discriminating colors and color patterns or boundaries in an RGB image signal and for generating signals indicating the color boundaries.

U.S. Pat. No. 3,986,777 describes a tristimulus colorimeter which measures the red, green and blue light reflected from a sample. The sample is illuminated through a probe by a light source having a satisfactory uniform distribution of light over the visible spectrum. Light reflected from the sample through the probe passes through a rotating color filter wheel, which is synchronized with a digital voltmeter, to a photosensitive diode.

U.S. Pat. No. 4,096,217 describes a method of using a tristimulus colorimeter in making artificial teeth.

Each of the preceding examples describes technology, apparatuses or methods for making color measurements or comparisons. However, none of them describes the invention of a small, hand-held and inexpensive colorimeter which can permit an operator unskilled in color analysis to quickly and objectively make consistent color measurements and comparisons.

An object of the present invention is to provide a high-resolution colorimeter system, utilizing solid-state opto-electronic technology, for measuring and characterizing tooth and prosthesis colors.

BRIEF SUMMARY OF THE INVENTION

The invention is a colorimeter especially suited for dental applications comprising a hand-held probe, similar in size to a dental drill, attached by an electrical cable to a small display module.

The colorimeter provides the capability for measuring the colors of a number of points along a line on the surface of an object such as a tooth. A measurement is made while placing the tip of the probe against, or in close proximity to, the surface of the object. The display module to which the probe attaches contains a microprocessor and provides a control, display and data interface to the operator. The display module can be adapted for fastening to the wrist of the operator thereby leaving both hands free to manipulate the probe and other tools. The colorimeter is particularly well suited for measuring the color of teeth in a dentist's office in preparation for making dental prostheses which accurately match the color of natural teeth. The colorimeter generates from a single measurement an array of color data points measured along a line on the surface of an object. From those data points, the processor can perform statistical analysis yielding a single color value, generate and display a color profile along a line, compare measured values with a preloaded table of values, or upload color data to a remote location for laboratory or manufacturing purposes. The colorimeter can also use variations in the color values measured along a line to identify boundaries of areas on a surface. For example, the color profile can be used to identify the gum line on a tooth.

As used herein, the term "color value" means any representation of a measured color. For example, it can be a single number or a symbol, or it can be a group of numbers or symbols such as three RGB ratios, a set of tristimulus values, or a set of statistical parameters representing a vector. A color value can also be represented by the result of a comparison of measured color values to stored color values.

The probe comprises multiple light emitting diodes (LEDs) for successively emitting light of different colors toward a surface, a linear array of light sensors for receiving light reflected from the surface, and a lens for directing light from the target to the array, all contained within the probe itself.

The LEDs are arranged in a line near the probe tip and coupled to the target via a light pipe. The LEDs emit preferably three—red, green and blue (RGB)—primary colors. The three colors are preferably discrete in the sense that their wavelengths do not overlap. One or more LEDs of each color may be used depending on the efficiency of the LEDs of different colors. Additional LED colors may be used for greater accuracy if needed.

The lens is preferably a flat wafer similar in shape to a thin cross-section of a conventional lens. The lens focuses an image of the illuminated surface onto the linear photosensor array.

The photosensor array is a relatively broad-spectrum integrated circuit device which is sensitive to all the wavelengths emitted by the LEDs. In operation, the LEDs are illuminated sequentially by color and the light of each color reflected from the target is sensed by the array and represented by a vector of electrical signals.

The probe also contains circuitry for interfacing to the optical devices and for coupling the reflected light signals to the display module.

The display module preferably provides a liquid crystal display (LCD) and control buttons for operating the colorimeter. The module contains a microprocessor, memory and associated support hardware for processing, storing and displaying digital data from the probe, as well as preferably rechargeable batteries for providing power to itself and to the probe. The microprocessor can run software routines for calibrating the color measurement devices and for comparing measured values with stored values. The stored values can be used to compare or match the color of dental prostheses to the measured colors of natural teeth. The processor can be used to detect color boundaries such as a gumline by analyzing the spatial profile of data obtained from the linear array.

The colorimeter may also comprise a cradle for storing the probe and display module when not in use. The cradle may provide a battery charger and the capability of uploading or downloading data from a remote location via cable, infrared (IR) or radio-frequency (RF) links. The cradle may also provide references for calibrating the colorimeter.

The LEDs are strobed, one at a time, and light from each is reflected from a tooth and received by a linear photosensor array. The photosensor array produces an electrical analog signal which is applied to an analog-to-digital converter (ADC). The ADC converts the analog signal to digital values representing the reflected light intensity. The digital values for each color are stored in a storage device. The stored values are processed by a microprocessor as necessary to specify the color of a prosthesis which will match the color of the tooth. When the colors of all areas of interest on a tooth are measured, the results can be compiled and sent to a custom prosthesis manufacturer. Alternatively, the results can be compared with a look-up table of standard color values stored in the colorimeter's memory. In the latter case, when a match is found this standard color identification number is displayed on a display panel.

The colorimeter is calibrated every time that it is turned on to insure accurate measurements. Reflectance measurements of a white calibration reference are made and stored for use in processing the data when data measurements are made.

New reference data on comparison samples can be loaded into the colorimeter whenever they are available. The technique for the upgrade can either be done via modem, floppy disk or hardware.

DETAILED DESCRIPTION OF THE INVENTION

In the drawings, like reference numerals indicate like features; and, a reference numeral appearing in more than one figure refers to the same element. The drawings and the following detailed descriptions show specific embodiments of the invention. Numerous specific details including materials, dimensions, and products are provided to illustrate the invention and to provide a more thorough understanding of the invention. However, it will be obvious to one skilled in the art that the invention may be practiced without these specific details.

Figure 1:
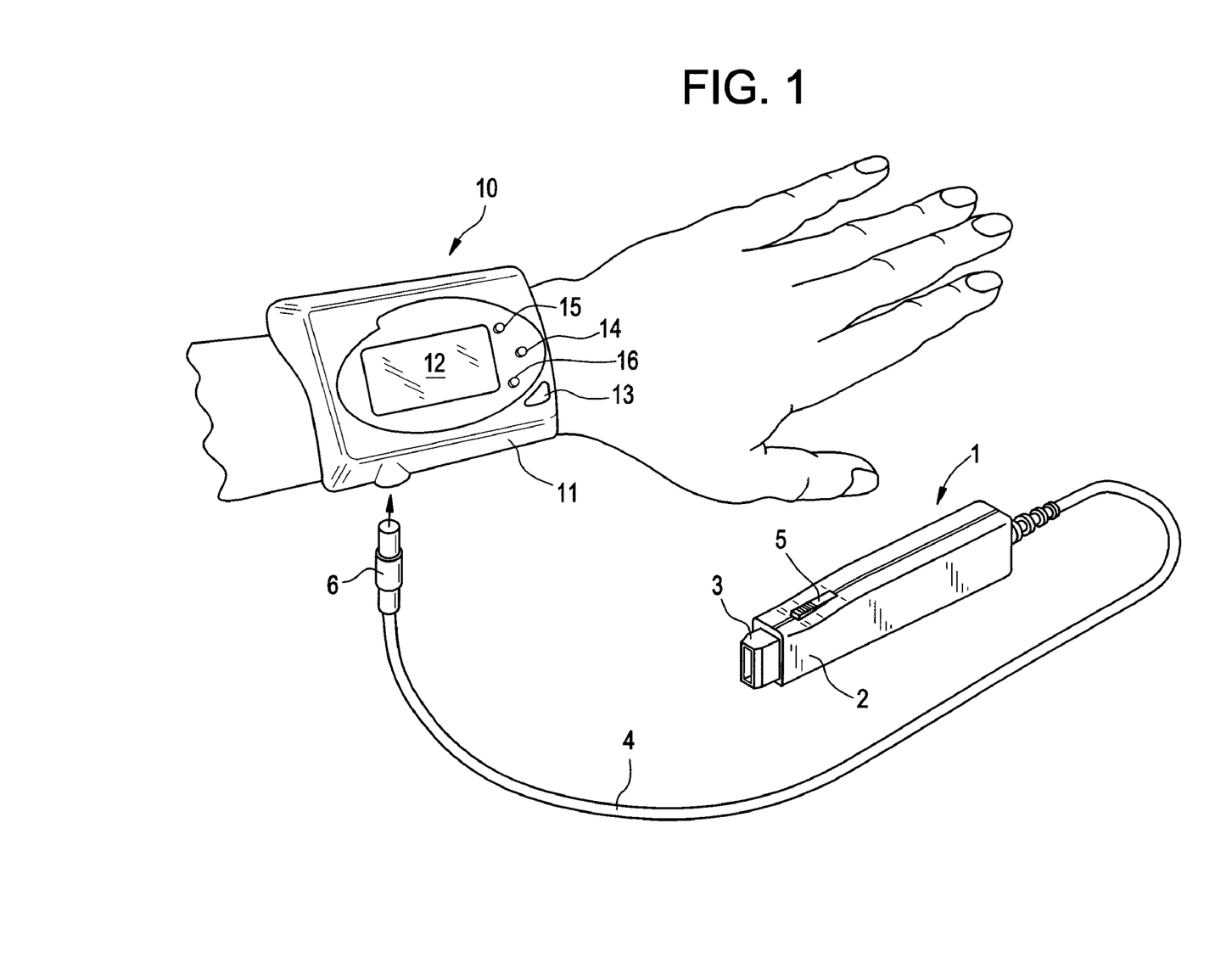
FIG. 1 is a drawing showing the components of the colorimeter.

An exterior view of the invention is shown in FIG. 1. The colorimeter comprises probe 1 and display module 10. Probe 1 further comprises probe body 2, probe tip 3, cable 4 and measure button 5. Display module 10 comprises body 11, display panel 12, power switch 13, and control switches comprising "menu select" button 14, "scroll up" button 15 and "scroll down" button 16. The colorimeter may also comprise an optional cradle (not shown) for storing the probe and display module.

The material of the probe body is preferably an impact-resistant polycarbonate. The probe is shaped to facilitate one-handed operation and is preferably less than 15 cm in length and less than 5 cm² in cross sectional area.

The material of display module body is preferably an impact-resistant polycarbonate. The module can be clipped into a mount or worn on the wrist to allow one hand to operate the colorimeter. The menu and scrolling buttons are preferably large and clearly marked to provide a friendly user interface.

Figure 2A:
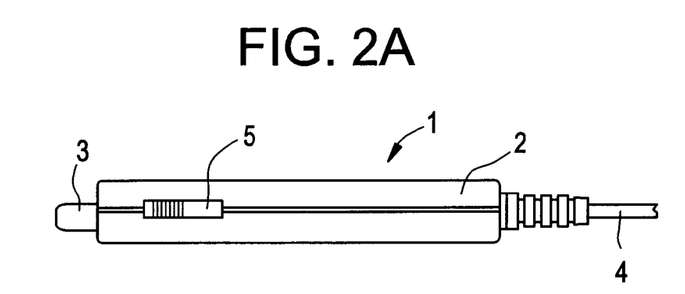
FIGS. 2A, 2B, 2C and 2D are top, side, bottom and end views of the probe.
Figure 2B:
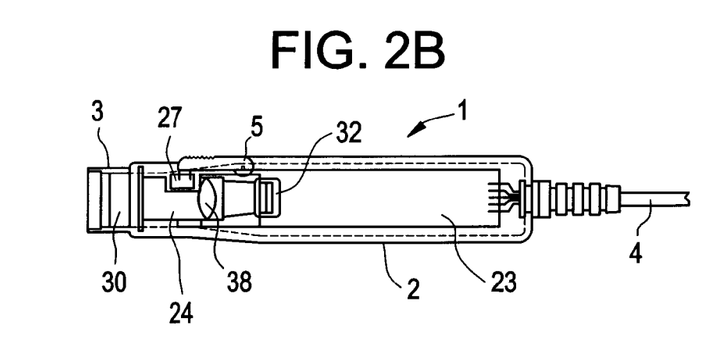
Figure 2C:
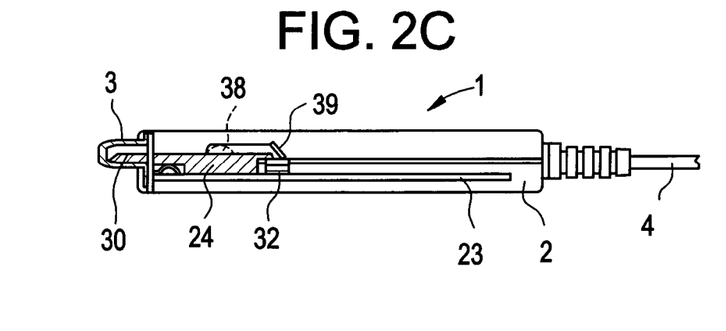
Figure 2D:
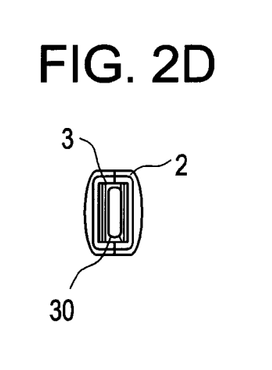

A top view of the probe is shown in FIG. 2A. Left side and bottom cross sectional views of the probe are shown in FIGS. 2B and 2C. An distal end view is shown in FIG. 2D. The probe 1 comprises probe body 2, probe tip 3, cable 4, measure button 5, light pipe assembly 30, lens 38, mirror 39, linear photosensor array 32, circuit board 23 and optics support 24. Measure button 5 is coupled to measure switch 27.

Figure 3A:
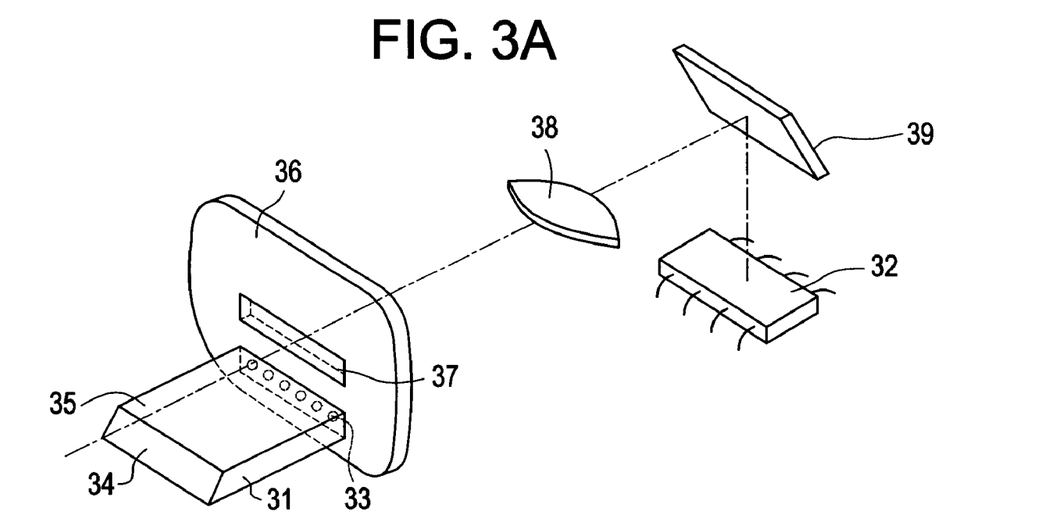
FIG. 3A is a schematic drawing of a first embodiment of the optical assembly.

FIG. 3A is a perspective drawing of the optical assembly. In FIG. 3A a light pipe assembly 30 is enclosed within probe tip 3 of FIGS. 2A–2D and comprises light pipe 31, LEDs 33, illumination surface 34, and baffle 35. The optics assembly also comprises optics circuit board 36 and aperture 37. Light pipe 31 has the shape of a truncated wedge with the illumination surface 34 on its distal end. LEDs 33 are abutted to, or imbedded in, the proximal end of light pipe 31. LEDs 33 are arranged preferably in a row and electrically connected to optics circuit board 36. Illumination surface 34 is preferably a diagonal section through pipe 31 and may be tilted inwardly toward the optical axis, with a diffusing surface finish, as shown in FIG. 3A or it may be tilted outwardly away from the optical axis with a smooth refracting surface. However, surface 34 may have a diffusing or refracting surface of any shape which provides adequate illumination of the target. The outer surface of pipe 31 may be coated or separated slightly from the interior surface of tip 3 to satisfy the index of refraction requirements for light pipe operation.

Figure 3B:
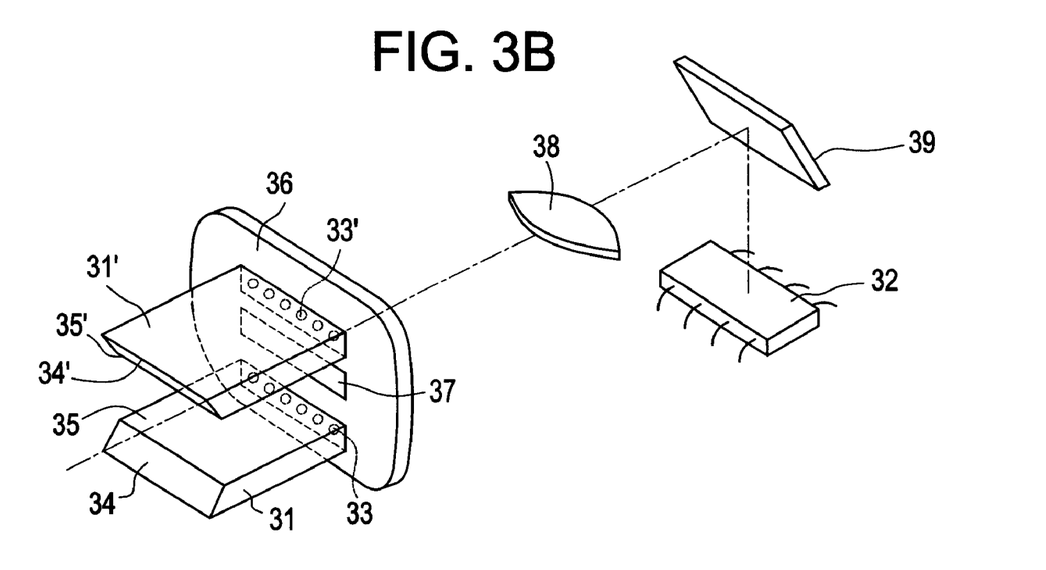
FIG. 3B is a schematic drawing of a second embodiment of the optical assembly.

FIG. 3B is a perspective drawing of an optical assembly having two light pipe assemblies 30 and 30' for use when a single light pipe assembly provides insufficient illumination.

Lens 38 is located to focus an image of a line on the target (the object plane) onto the light sensitive elements of photosensor array 32 (the image plane). Lens 38 may have the shape of a conventional lens or the shape of a slice through a conventional lens taken parallel to its axis. Mirror 39 permits mounting the photosensor array off the optical axis. The lens and mirror shapes and locations permit adjusting the optics for the desired magnification consistent with minimum probe size. Mirror 39 may be omitted if array 32 is located on the optical axis.

Light emitted from LEDs 33 is contained within light pipe 31 by total internal reflection (TIR) and guided through illumination surface 34 to illuminate the target. If surface 34 is an inwardly-tilted diffusing surface, light is scattered uniformly over the target. If surface 34 is an outwardly-tilted refracting surface, light is refracted onto the target. The angle and surface finish of surface 34 can be chosen by one of ordinary skill in the art to optimize the uniformity and intensity of the illumination of the target. Probe tip 3 shields the target from external ambient light. Light reflected from the target passes through aperture 37, lens 38 and is reflected off mirror 39 onto array 32. The dimensions of aperture 37 are chosen to prevent specular reflections from the target from reaching array 32. Baffle 35 prevents light from LEDs 33 from directly reaching array 32. The baffle may be a coating on pipe 31 or a separate opaque panel. Coatings may be optionally applied to the lens or the mirror to pass only light having desired wavelengths and to block light having wavelengths outside the spectrum of interest. Optical filters may be also be used in the photosensor array light path for this purpose. For example, filters or coatings may act as bandpass filters which block infrared and ultraviolet light or may comprise one or more notch filters to provide separation between the wavelengths emitted by the different color LEDs. A notch filter is a filter which blocks light of a narrow band of wavelengths.

Preferably, lens 38 is an achromatic lens which corrects on-axis spherical and chromatic aberrations. The preferred optical magnification is 0.5. At this magnification, for a linear photosensor array providing a resolution of 150 dots per inch (DPI), the maximum object size is 16 mm.

The wafer shape of the lens is chosen to reduce the width of the probe. The preferred sensing area is roughly rectangular (12.5 mm in height by 1.5 mm in width) and the preferred width of the lens, looking down along the optical path, is 2.0 mm. This reduces the overall width of the probe as compared to a circular lens. The lens 38 and mirror 39 are mounted to an optics support 24 which provides an integral optical assembly.

The colorimeter uniformly illuminates an oblong region, on a target, that is parallel to and in contact with the contact plane of the outer sleeve. The LEDs, preferably comprising two red (655 nm), two green (565 nm), and two blue (430 nm) LED's, are preferably arranged in a linear pattern and spaced about 1.25 mm apart from one another. The probe tip 3 locates the point of contact with the target and shields the system from ambient light. The light pipe baffle 35 and rectangular aperture 37 prevent direct light from the LED's reaching the photosensor array. The signals generated by the array result only from light reflected by the target.

The aperture preferably prevents light entering at more than about 5 degrees from the optical axis from reaching the array. The aperture can include an optical filter to attenuate light having a wavelength that is more than about 50 nm above or below a nominally-measured wavelength.

The probe tip comprises a sleeve that is sufficiently flexible and conformable to facilitate fairly tight contact with the target surface. Opaque materials are preferred for this purpose (e.g., an opaque vinyl or rubber), sufficiently flexible and conformable to facilitate fairly tight contact with the target surface. Preferably, the sleeve is sufficiently flexible to conform to an irregular surface. In medical or dental applications, the sleeve should be sanitary and disposable. A suitably-designed sleeve is preferably stiff enough to control the target position relative to the light sources and photosensor array. The probe tip can be manufactured so that it is either expendable or can be autoclaved. An alternative method of maintaining sterilization is to use a thin plastic transparent cover over the tip. The probe tip preferably includes a hook or protrusion on its distal edge for aligning the edge of the probe tip with the tip of a tooth.

In operation, probe tip 3 is placed against the target and the LEDs of each color are illuminated in sequence. As the target is illuminated by each color, a portion of the reflected light is captured by the photosensor array which produces a vector of electrical signals representing the intensity of the reflected light along a line on the target. As used herein, a vector means an array of values wherein each value corresponds to one of the photosensor locations in the linear photosensor array.

Figure 4:
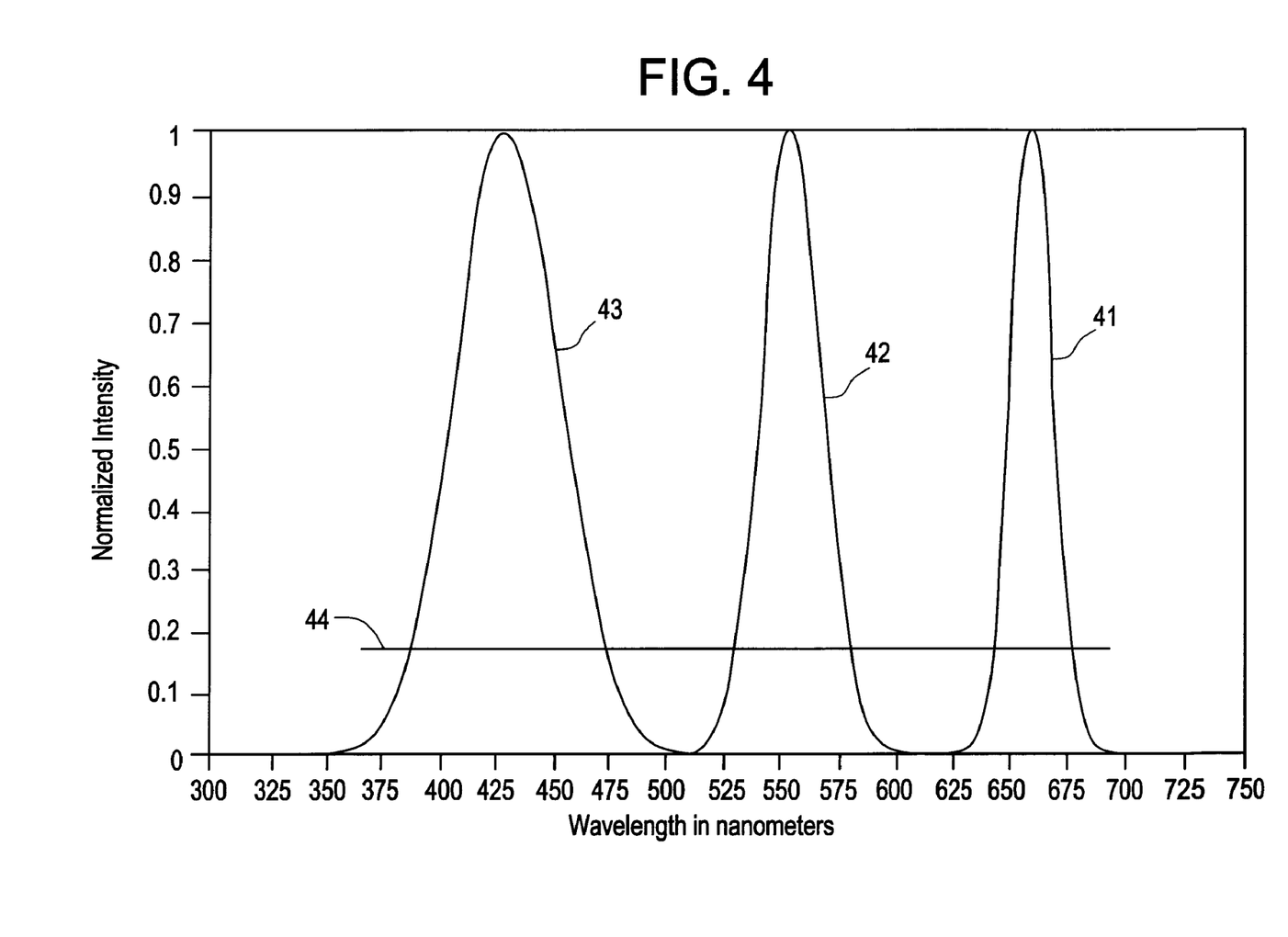
FIG. 4 is a plot of light intensity vs. wavelength for the illumination system.

An exemplary plot of light intensity vs. wavelength for three LED colors is shown in FIG. 4. This example shows spectral profiles for a red LED 41, a green LED 42 and a blue LED 43. In this plot, the three profiles are discrete; that is, they do not overlap. However, as known to those skilled in the art, LEDs having profiles with different peak wavelengths and different widths may be used. The inherent emission profiles of the LEDs can be altered by optical filters or coatings on the LED encapsulations. Also, the effective profile widths can be altered by the use of optical notch filters in the photosensor array light path or by setting a detection threshold 44 either within the signal path from the photosensor array to the microprocessor or in the digital processing routines of the microprocessor. Such a threshold can be set to disregard light intensities below the threshold and thereby eliminate wavelengths outside the threshold. A different threshold can be specified for each color and stored in memory. The stored threshold values can be used directly by the microprocessor or converted by a digital-to-analog converter (DAC) to an analog signal for use by a comparator in the analog signal path.

To compensate for variations in sensitivity of the photosensor array across the wavelength spectrum and for differences in the efficiency of different LEDS, the light output of each of the LEDs may be adjusted by varying its current.

Figure 5:
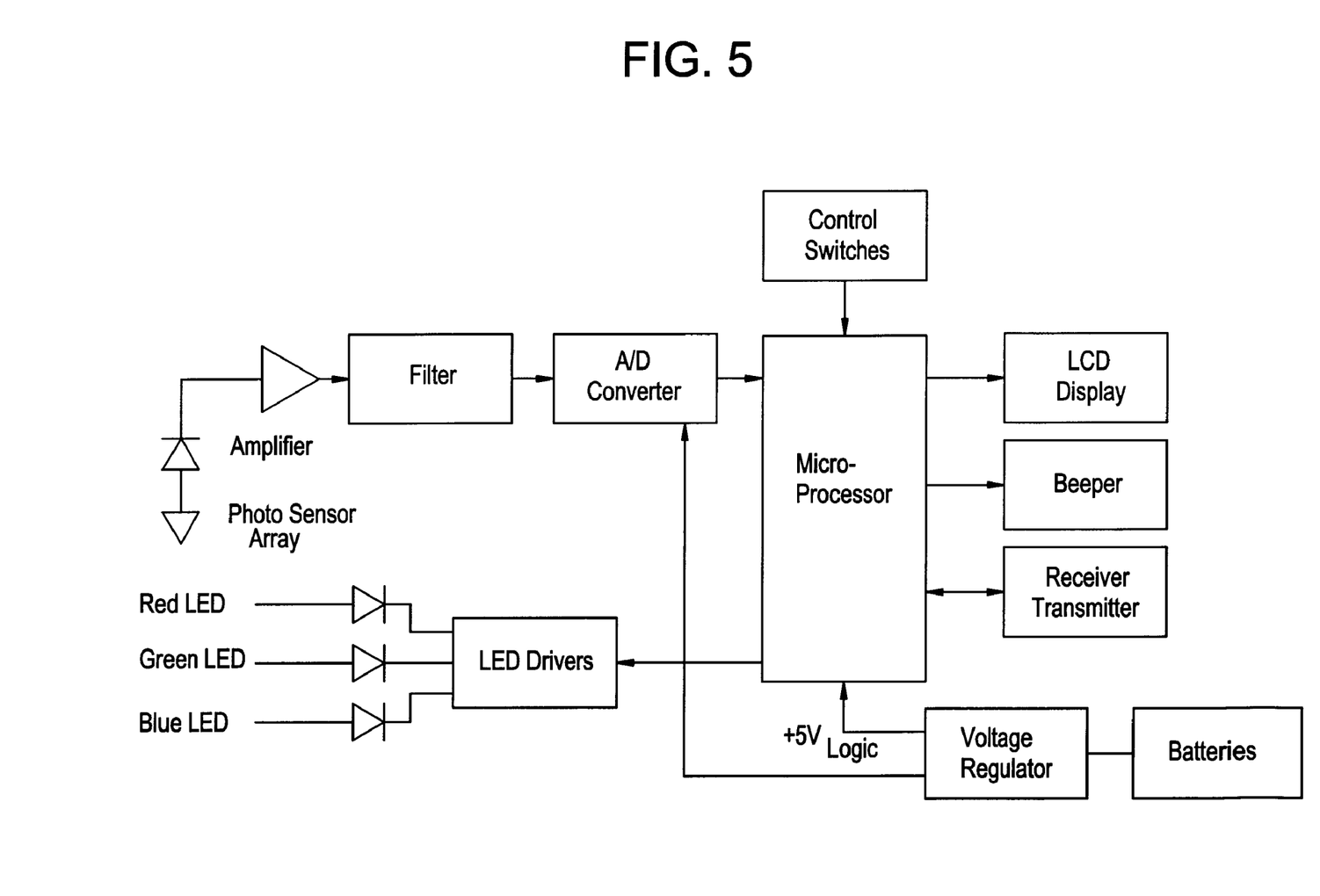
FIG. 5 is a block diagram of the circuits in the colorimeter.

A block diagram of the circuits contained in the colorimeter is shown in FIG. 5. Although the circuits are shown as separate functional blocks, it will be recognized by those with ordinary skill in the art that some or all of the functions can be combined in integrated circuits. The term microprocessor as used herein includes the family of devices known as microcontrollers.

Each time the colorimeter is turned on, and prior to its operation, a calibration sequence is performed. This consists of measuring the known reflectance of a substantially white reference surface using all the colors in the probe. In some applications, the calibration may also include measuring the reflectance of a black reference.

The measurement sequence comprises sending a short current pulse to each LED of a color to illuminate the tooth. Reflected light from the tooth is focused onto the photosensor array which converts the light falling on each element of the array into an electrical representation of its intensity. After the array has been exposed to the reflected light, the array generates a vector of electrical signals representing the intensity of the light distributed across the array. The signals are coupled to an analog-to-digital converter (ADC) that converts the analog values into a digital signal comprising a vector of digital values which are then stored at a particular location in the storage device. This process is then repeated for each of the LED colors in the system.

Current is preferably supplied to the LEDs in short pulses to minimize self-heating and the resulting change in efficiency. If necessary to enhance measurement accuracy, multiple short pulses can be used for a single measurement and the results averaged or otherwise statistically analyzed.

When all three color measurements are made for an array of points, the microprocessor computes the ratios of the measured values to the calibration values for all the points on the line.

As used herein, a color ratio is defined as the ratio of the intensity of the light reflected onto each photosensor element from a target, whose color is being measured, to the intensity of the light reflected onto each photosensor element from the white calibration reference. When a black (or dark) reference is used, the color ratio is the ratio of the target intensity to the difference in intensity between the white and black (or dark) references. A color ratio is preferably generated for each photosensor element in the array and for each LED color used in the measurement; that is, the number of color ratios generated from a single linear measurement is equal to the number of LED colors used multiplied by the number of photosensor elements in the linear photosensor array.

After the first line of points is measured, the probe can be moved to another location and the sequence repeated.

Figure 8A:
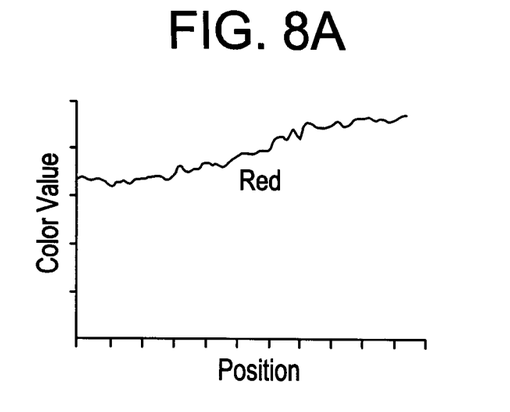
FIGS. 8A, 8B and 8C are reflectance vs. position plots for three colors.
Figure 8B:
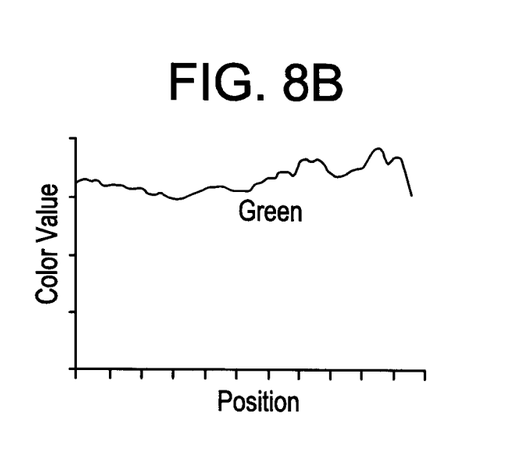
Figure 8C:
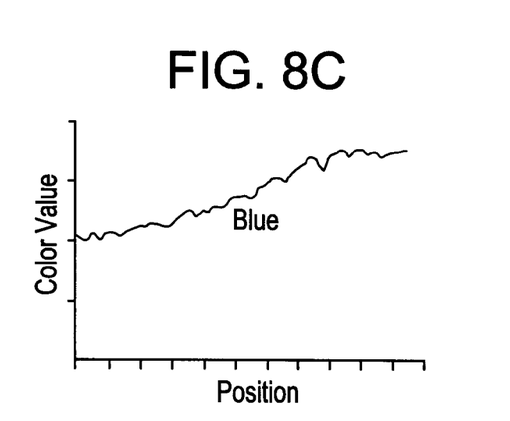

Color values are plotted for vectors produced by red, green and blue illumination in FIGS. 8A, 8B and 8C, respectively, as an example of the color variation along a line on a tooth measured by the invention. Plots of vectors such as this can be provided on the display panel of the invention by those of ordinary skill in the art.

When all the points are measured and the color ratios calculated, the color values for each point can be compared with the color values in a stored look-up table. When a close match is found, its identification can be shown on the display panel.

A set of color values can be translated into a set of coordinates in several accepted color characterization systems. A color value for use in a particular industry could have its coordinate system correlated to color index schemes accepted in that industry. Some such systems are qualitative, such as the color swatch system for characterizing flower colors established by the Royal Horticultural Society. Others are quantitative, such as the x, y, and Y color coordinate system explained in Billmeyer & Saltzman, *Principles of Color Technology* 43 (1966).

Although the invention encompasses monochromatic, discrete-color, and white light sources, emitted colors are referred to as having a nominal wavelengths, and (optionally) some distribution of light intensity at other wavelengths. Various intensity distributions may prove advantageous for a product designer implementing the current invention, depending on component availability or matching to the receptors in the human eye. See, e.g., W. D. Wright, *The Measurement of Color* 69 (1969) for further discussion of this concept. A two-color light source system may be most advantageous for a particular model of probe, based on a designer's empirical knowledge about the intended use: The color of a tooth, for example, can generally be measured adequately by red and yellow light sources.

A database can be used to predict a mixture of ingredients to achieve a desired final color. To accomplish this, color values of a variety of mixtures of pigmented components are stored in the database, which contains information such as ingredient ratios and color values measured before and after curing. By interpolation methods known in the software arts, a computer can use these data to calculate the respective amounts of uncured ingredients and predict the uncured color coordinates of the mixture. The color values of the mixed ingredients can be measured before and after curing, thus serving as a quality control mechanism at several steps in the manufacture of products such as dental prostheses.

The probe can be precisely positioned on a tooth by a protrusion on the edge of the probe tip before a measurement sequence or the probe can be positioned approximately during the measurement and its precise position detected after the measurement by analyzing color value differences along a vector.

The colorimeter requires a color calibration process executed with sufficient frequency to compensate adequately for component deterioration. Preferably, a clean white matte calibration sample is kept in an enclosure, e.g., within an enclosure or cavity in a cradle, to protect it from dust, scratching, or loss. For example, in the cradle an external lever pivots the calibration sample such that it will reflect light from the colorimeter's sources toward its sensing aperture.

While the invention is particularly suited to measuring regions of color, especially for samples of mixed color, other scientific uses are also feasible. For example, in forensics applications where color is important, a forensics expert could use the invention to confirm the origin of ink on a piece of white paper, even where chemical analysis is not feasible.

The invention can also employ predetermined limits based upon what is known about the color of objects whose colors are to be measured or filtered out. In the dental arts, for example, healthy gum tissue is known to be various hues of pink. An embodiment of the invention uses software to distinguish between gum colors and tooth colors. For example, the programmer selects a minimum color value of red and/or a maximum color value of green to ascertain where a transition occurs between tooth and gum. Using the gumline or the top of a tooth as a baseline, the invention thus permits consistent measurements of tooth color that are repeatable from one measurement to the next. This is useful in measuring the desired coloring of an adjacent tooth for the purpose of manufacturing a dental prosthesis. It is also useful to measure the effectiveness of whitening treatments quantitatively.

The invention preferably incorporates means for excluding measurement data that do not fall within specific limits. These limits can be applied at the time of measurement by analog comparators or later by software routines. The former can be implemented by receiving inputs from a voltage reference and from an analog signal representing the reflected light.

Software processes can provide threshold modifications, complex selection criteria, and complete data acquisition and testing. All three measurements corresponding to a single point on the target can be discarded if both neighboring points differ by more than a specific amount. This is advantageous for irregular surfaces (to account for intermittent occurrences of specular reflection on an irregular shiny surface) and for dusty environments (to account for measurements influenced by extraneous particles). The software selects a representative value such as a median, for a given set of measured points. A sum of the RGB measurements (R+G+B) is used as a measure of brightness for such a computation. The software evaluates deviations upward from that value as a measure of color uniformity or as a trigger for a software routine that detects the presence of particular colors. Software also provides the capability of differentiating tooth colors from gum or background colors and selecting only the tooth color values from a vector containing gum and background color values.

The invention may optionally comprise a cradle (not shown) for holding the display module and probe when the colorimeter is not in use. The cradle provides for battery charging, receiving data from the display module, uploading received data to a remote computer, and acting as a calibration station for the colorimeter. The cradle includes the calibration references.

When a measurement is made, the red, green, and blue LED's are strobed in sequence. The reflected light of each of the three colors is collected by the photosensor array and a representative electrical signal is generated. Ratios of the three signals are calculated and the ratios are compared to those stored in a stored look-up table by the microprocessor. When a color match is found, the information is displayed on the colorimeter's display module.

The user may have the option of transmitting the color match data directly to the cradle and then to a computer via an RS232 I/O serial port from the cradle. The cradle may contain an IR or RF link for exchanging data with the colorimeter's display module.

When first turned on, the colorimeter performs a self-diagnostic test to ensure proper operation. After the completion of a successful diagnostic test, the user is directed to calibrate the colorimeter. Upon completion of the calibration step, the can initiate a measurement sequence.

To initiate a measurement, the user only needs to actuate the "measure" button on the probe. The reflectance measurements of red, green, and blue are processed, then stored. Upon the successful completion of processing the third value, the three values, one for each color, are compared to values in look-up table stored in the system's memory. When the values match within the range of a stored color code number, the color code number is displayed on the display module. The user then has the option of transmitting the data to the cradle, or taking another measurement, or turning off the colorimeter.

The sequence for color matching using the colorimeter is:

When first turned on, the colorimeter prompts the user to calibrate to a white reference and optionally to a black reference. It does not matter if the display module is removed from the cradle to perform this operation. The user applies the probe tip to the white reference, then depresses the "measure" button until the "end of measurement" beeper sounds. The user repeats this step to calibrate to the black reference if one is used. After these steps the calibration data resides in the memory of the display module. This calibration data will be used to compute the ratios for all future measurements until the power is turned off. The colorimeter must be calibrated each time it is turned on.

Data may be taken at this point by placing the probe against the tooth and depressing the "measure" button on the probe. Each time the "measure" button is depressed, the colorimeter preferably will take 5 sets of data measurements for each color in rapid succession, process them, and activate the "end of measurement" beeper. At this time, the data is processed and compared to a look-up-table for a color match. The color match can then be displayed on the display module.

Choosing the "transmit data" function on the display module transmits the measurement data to a remote computer.

Figure 6:
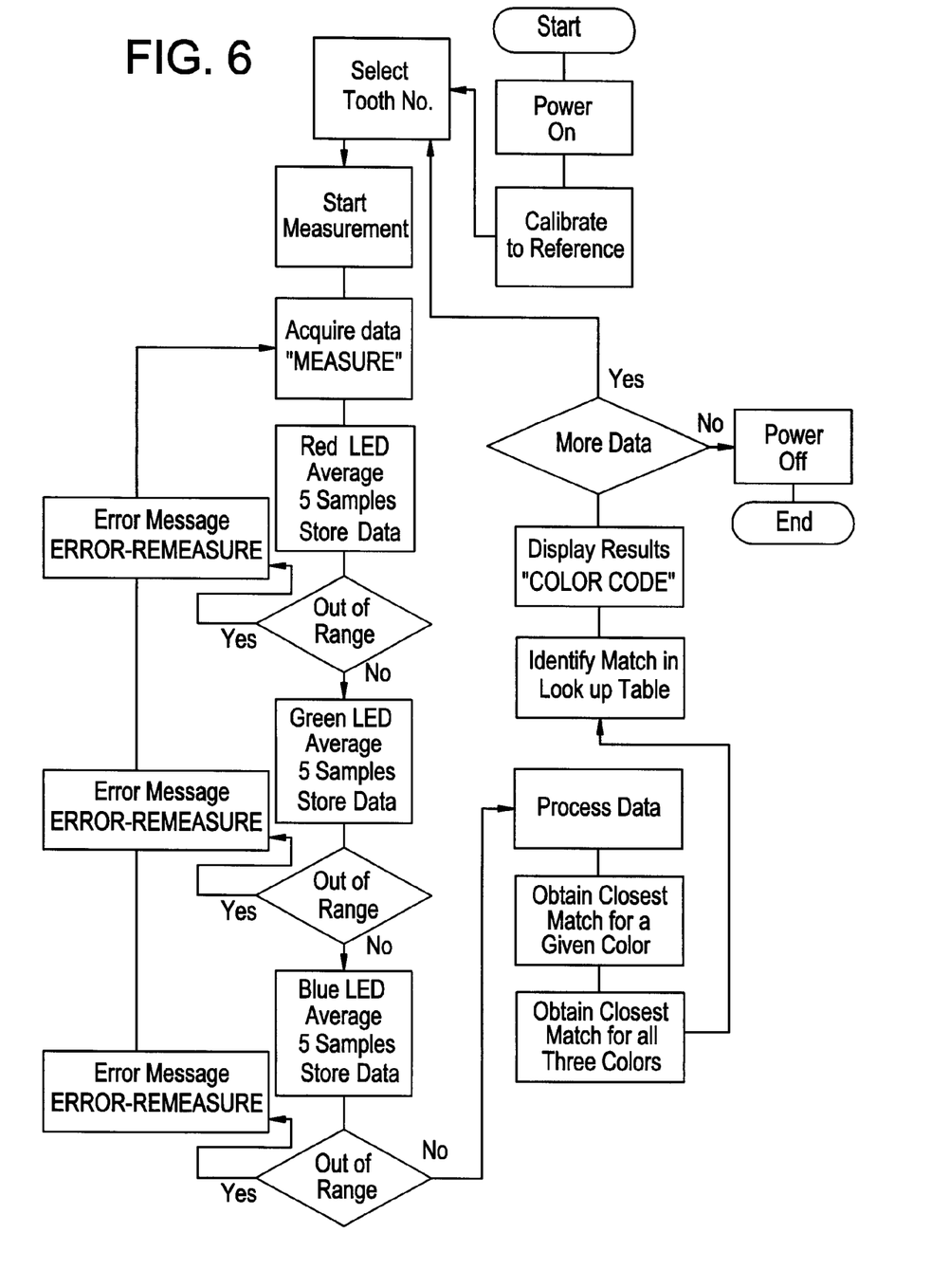
FIG. 6 is a flow chart of the colorimeter operation.

FIG. 6 is a software flow diagram illustrating a measurement sequence.

Figure 7:
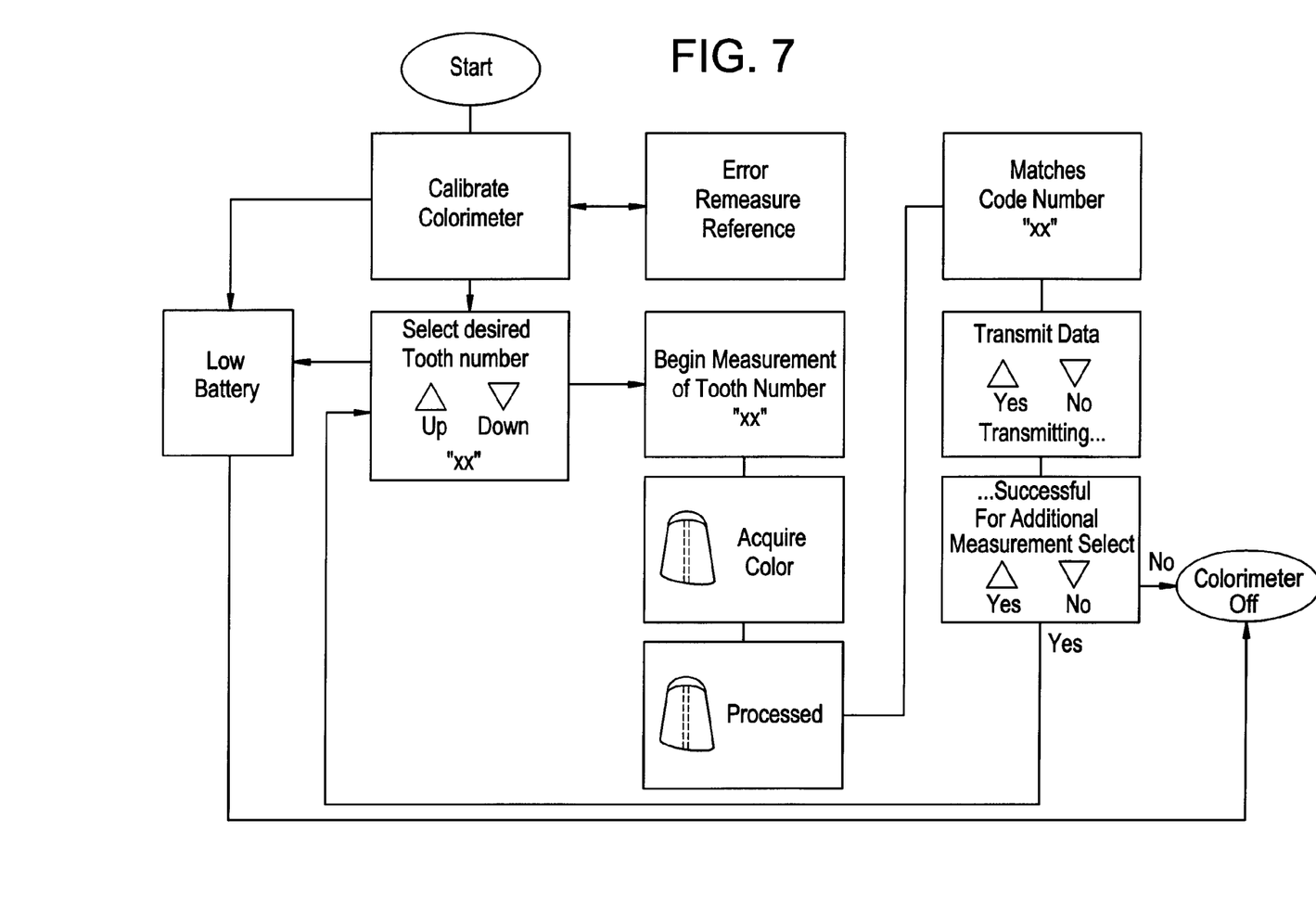
FIG. 7 is a state diagram of colorimeter display images.

The display panel provides the user with the information required to select the desired function. FIG. 7 is an exemplary state diagram of images that can be presented to an operator by the display panel of the invention. In the diagram, rectangles indicate displays and ovals indicate user inputs.

When the colorimeter is not in use, the user can park the display module and probe in the cradle. The display module can be turned off and the cradle may remain on to charge the batteries.

While the invention has been described above with respect to specific embodiments, it will be understood by those of ordinary skill in the art that various changes in form and details may be made therein without departing from the spirit and scope of the invention.

All references mentioned herein are hereby incorporated by reference to the extent that they are not inconsistent with the present disclosure.

What is claimed is:

1. A dental colorimeter, for measuring the color of a target, comprising:
   a miniature probe, containing:
      a light pipe;
      at least two different-colored light sources, optically coupled to said pipe;
      a lens; and
      a linear photosensor array, optically coupled to said lens; and
   a display module, coupled to said probe, further comprising:
      a microprocessor, coupled to said sources and said array; and
      a display panel, coupled to said microprocessor.

2. A colorimeter as in claim 1 further comprising an electrical cable connected to said probe and to said module, for coupling said probe to said module.

3. A colorimeter as in claim 1 wherein said light sources are LEDs.

4. A colorimeter as in claim 1 wherein said light sources emit red, blue and green light.

5. A colorimeter as in claim 1 wherein said light sources can be sequentially illuminated.

6. A colorimeter as in claim 1 wherein said probe has a length not exceeding 15 cm and a cross-sectional area not exceeding 5 $cm^2$.

7. A colorimeter as in claim 1 wherein said light sources emit wavelengths which do not overlap.

8. A colorimeter as in claim 1 further comprising an optical filter between said target and said array.

9. A colorimeter as in claim 1 further comprising a memory for storing measured values.

10. A colorimeter as in claim 1 further comprising a memory for storing computational routines and comparison data.

11. A colorimeter as in claim 1 further comprising a program for computing a ratio of light intensity reflected from a target to light intensity reflected from a substantially white reference.

12. A colorimeter as in claim 11 further comprising a program for comparing said ratio with a stored value.

13. A colorimeter as in claim 1 further comprising a stored calibration routine.

14. A colorimeter as in claim 1 further comprising a stored measurement routine.

15. A colorimeter as in claim 1 further comprising a stored comparison routine.

16. A colorimeter as in claim 1 further comprising a routine for displaying a spatial plot of a vector.

17. A colorimeter as in claim 16 wherein said vector comprises a vector of ratios.

18. A colorimeter as in claim 1 further comprising an optical filter for shielding said array from undesired wavelengths.

19. A colorimeter as in claim 1 further comprising a notch filter for shielding said array from overlapping wavelengths emitted by said light sources.

20. A colorimeter as in claim 1 wherein said colorimeter includes a threshold process for eliminating overlapping wavelengths emitted by said light sources.

21. A colorimeter as in claim 1 wherein said colorimeter includes a routine for selecting, according to color values, a number of color values from a vector.

22. A colorimeter as in claim 1 further comprising a battery contained within said display module.

23. A colorimeter as in claim 1 further comprising a wrist strap attached to said display module.

24. A colorimeter as in claim 1 further comprising a link for exchanging data with a computer.

25. A colorimeter as in claim 1 further comprising a removable probe tip.

26. A colorimeter as in claim 1 further comprising a disposable probe tip.

27. A colorimeter as in claim 1 further comprising a probe tip having a protrusion for alignment.

28. A colorimeter as in claim 1 further comprising a measure switch in said probe.

29. A colorimeter as in claim 1 further comprising a control switch in said display module.

30. A colorimeter as in claim 1 wherein an illumination surface of said light pipe is a diffusing surface.

31. A colorimeter as in claim 1 wherein an illumination surface of said light pipe is a refracting surface.

32. A method, for measuring the color of a target, comprising the steps of:
   providing a colorimeter as in claim 1:
      sequentially illuminating a reference target with a plurality of colors;
      measuring the light reflected from the reference target for each of the colors;
      generating and storing a reference value representing the light measured for each of the colors;
      sequentially illuminating the target with a plurality of colors;
      measuring the light reflected from the target for each of the colors;
      generating and storing a color value representing the light measured for each of the colors; and
      computing a ratio of each color value to each reference value.

33. A method as in claim 32 further comprising the steps of:
   displaying a symbol representing each ratio on the display panel.

34. A method as in claim 32 further comprising the steps of:
   comparing each ratio with a stored ratio; and
   displaying a symbol representing a result of each comparison on the display panel.

35. A method as in claim 32 further comprising the step of selecting from a vector, according to color values, a number of color values from a vector.

36. A method as in claim 32 further comprising the step of displaying a plot of a vector on the display panel.

* * * * *